(12) United States Patent
Vardi et al.

(10) Patent No.: US 6,884,258 B2
(45) Date of Patent: Apr. 26, 2005

(54) BIFURCATION LESION STENT DELIVERY USING MULTIPLE GUIDEWIRES

(75) Inventors: Gil M. Vardi, Town and Country, MO (US); Charles Davidson, Winnetka, IL (US); Eric Williams, Fairfield, CA (US)

(73) Assignee: Advanced Stent Technologies, Inc., Pleasanton, CA (US)

( * ) Notice: Subject to any disclaimer, the term of this patent is extended or adjusted under 35 U.S.C. 154(b) by 320 days.

(21) Appl. No.: 09/794,740

(22) Filed: Feb. 26, 2001

(65) Prior Publication Data

US 2001/0049548 A1 Dec. 6, 2001

Related U.S. Application Data

(63) Continuation of application No. 09/663,111, filed on Sep. 15, 2000, which is a continuation-in-part of application No. 09/614,472, filed on Jul. 11, 2000, now abandoned, and a continuation-in-part of application No. 09/455,299, filed on Dec. 6, 1999, now Pat. No. 6,692,483, which is a continuation-in-part of application No. 09/325,996, filed on Jun. 4, 1999, now abandoned.

(51) Int. Cl.$^7$ .................................................. A61F 2/06
(52) U.S. Cl. ..................... 623/1.11; 623/1.34; 623/1.35; 606/108; 604/98.01
(58) Field of Search ............................. 623/1.11, 1.23, 623/1.34, 1.35; 606/108, 153, 195; 604/98.01, 103.04, 264, 523

(56) References Cited

U.S. PATENT DOCUMENTS

| | | |
|---|---|---|
| 1,596,754 A | 8/1926 | Mochelle |
| 3,657,744 A | 4/1972 | Ersek |
| 3,872,893 A | 3/1975 | Roberts |
| 4,140,126 A | 2/1979 | Choudhury |
| 4,309,994 A | 1/1982 | Grunwald |
| 4,410,476 A | 10/1983 | Redding et al. |

(Continued)

FOREIGN PATENT DOCUMENTS

| | | |
|---|---|---|
| CA | 2318314 | 7/1999 |
| DE | 9014845.2 | 2/1991 |
| DE | 29701758 | 5/1997 |

(Continued)

OTHER PUBLICATIONS

SCIMED Life Systems, Inc.—TRIO™ 14 PTCA Catheter, Re–engineering Over–the–Wire Balloon Technology, Company Brochure, 1994.

Caputo et al., "Stent Jail: A Minimum–Security Prison" The American Journal of Cardiology, (1996) 7:1226–1230.

Fischman et al., "A Randomized Comparison of Coronary–Stent Placement and Balloon Angioplasty in the Treatment of Coronary Artery Disease" The New England Journal of Medicine, (1994) 331(8): 496–501.

(Continued)

*Primary Examiner*—Paul B. Prebilic
(74) *Attorney, Agent, or Firm*—Patton Boggs LLP (57) ABSTRACT

A method for placing a stent into a main vessel such that the stent side hole aligns with a branch vessel ostium comprises inserting a main vessel guidewire into the main vessel and a branch vessel guidewire into the main vessel until a distal end of the branch vessel guidewire passes into the branch vessel. A catheter system is positioned over the main vessel guidewire and the branch vessel guidewire. The catheter system is advanced over the guidewires until the catheter body passes beyond the ostium of the branch vessel and the side member extends into the branch vessel. Marker separation is observed to indicate the catheter body passed beyond the ostium and the side member extends into the branch vessel. The balloon is inflated to deploy the stent with the side hole being aligned with the ostium. The balloon is deflated, and the catheter system is withdrawn.

4 Claims, 7 Drawing Sheets

U.S. PATENT DOCUMENTS

| | | |
|---|---|---|
| 4,413,989 A | 11/1983 | Schjeldahl |
| 4,421,810 A | 12/1983 | Rasmussen |
| 4,453,545 A | 6/1984 | Inoue |
| 4,503,569 A | 3/1985 | Dotter |
| 4,552,554 A | 11/1985 | Gould et al. |
| 4,681,570 A | 7/1987 | Dalton |
| 4,689,174 A | 8/1987 | Lupke |
| 4,731,055 A | 3/1988 | Melinyshyn et al. |
| 4,733,665 A | 3/1988 | Palmaz |
| 4,739,762 A | 4/1988 | Palmaz |
| 4,759,748 A | 7/1988 | Reed ........................ 604/95 |
| 4,762,128 A | 8/1988 | Rosenbluth |
| 4,769,029 A | 9/1988 | Patel |
| 4,819,664 A | 4/1989 | Nazari |
| 4,872,874 A | 10/1989 | Taheri |
| 4,878,495 A | 11/1989 | Grayzel |
| 4,896,670 A | 1/1990 | Crittenden |
| 4,900,314 A | 2/1990 | Quackenbush |
| 4,906,244 A | 3/1990 | Pinchuk et al. |
| 4,909,258 A | 3/1990 | Kuntz et al. |
| 4,946,464 A | 8/1990 | Pevsner |
| 4,957,501 A | 9/1990 | Lahille et al. |
| 4,957,508 A | 9/1990 | Kaneko et al. |
| 4,964,850 A | 10/1990 | Bouton et al. |
| 4,983,167 A | 1/1991 | Sahota |
| 4,994,071 A | 2/1991 | MacGregor |
| 5,042,976 A | 8/1991 | Ishitsu et al. |
| 5,054,501 A | 10/1991 | Chuttani et al. |
| 5,059,177 A | 10/1991 | Towne et al. |
| 5,061,240 A | 10/1991 | Cherian |
| 5,064,435 A | 11/1991 | Porter |
| 5,085,664 A | 2/1992 | Bozzo |
| 5,102,403 A | 4/1992 | Alt |
| 5,102,417 A | 4/1992 | Palmaz |
| 5,104,404 A | 4/1992 | Wolff |
| 5,117,831 A | 6/1992 | Jang |
| 5,122,125 A | 6/1992 | Deuss |
| 5,135,536 A | 8/1992 | Hillstead |
| 5,147,317 A | 9/1992 | Shank et al. |
| 5,159,920 A | 11/1992 | Condon et al. |
| 5,176,617 A | 1/1993 | Fischell et al. |
| 5,192,297 A | 3/1993 | Hull |
| 5,195,984 A | 3/1993 | Schatz |
| 5,211,683 A | 5/1993 | Maginot |
| 5,217,440 A | 6/1993 | Frassica |
| 5,222,971 A | 6/1993 | Willard et al. |
| 5,226,913 A | 7/1993 | Pinchuk |
| 5,234,457 A | 8/1993 | Andersen |
| 5,236,446 A | 8/1993 | Dumon |
| 5,244,619 A | 9/1993 | Burnham |
| 5,257,974 A | 11/1993 | Cox |
| 5,263,932 A | 11/1993 | Jang |
| 5,282,472 A | 2/1994 | Companion et al. |
| 5,304,220 A | 4/1994 | Maginot |
| 5,320,605 A | 6/1994 | Sahota |
| 5,324,257 A | 6/1994 | Osborne et al. |
| 5,337,733 A | 8/1994 | Bauerfeind et al. |
| 5,338,300 A | 8/1994 | Cox |
| 5,342,295 A | 8/1994 | Imran |
| 5,342,297 A | 8/1994 | Jang |
| 5,342,387 A | 8/1994 | Summers |
| 5,350,395 A | 9/1994 | Yock |
| 5,383,892 A | 1/1995 | Ansel et al. |
| 5,387,235 A | 2/1995 | Chutner |
| 5,395,332 A | 3/1995 | Ressemann et al. |
| 5,395,334 A | 3/1995 | Keith et al. |
| 5,404,887 A | 4/1995 | Prather |
| 5,409,458 A | 4/1995 | Khairkhahan et al. |
| 5,413,581 A | 5/1995 | Goy |
| 5,413,586 A | 5/1995 | Dibie et al. |
| 5,417,208 A | 5/1995 | Winkler |
| 5,425,765 A | 6/1995 | Tiefenbrun et al. |
| 5,437,638 A | 8/1995 | Bowman |
| 5,443,497 A | 8/1995 | Venbrux |
| 5,445,624 A | 8/1995 | Jimenez |
| 5,449,373 A | 9/1995 | Pinchasik et al. |
| 5,449,382 A | 9/1995 | Dayton |
| 5,456,694 A | 10/1995 | Marin et al. |
| 5,456,712 A | 10/1995 | Maginot |
| 5,456,714 A | 10/1995 | Owen |
| 5,458,605 A | 10/1995 | Klemm |
| 5,462,530 A | 10/1995 | Jang |
| 5,476,471 A | 12/1995 | Shifrin et al. |
| 5,489,271 A | 2/1996 | Anderson |
| 5,489,295 A | 2/1996 | Piplani et al. |
| 5,496,292 A | 3/1996 | Burnham |
| 5,505,702 A | 4/1996 | Arney |
| 5,507,768 A | 4/1996 | Lau |
| 5,507,769 A | 4/1996 | Marin et al. |
| 5,514,154 A | 5/1996 | Lau et al. |
| 5,514,178 A | 5/1996 | Torchio |
| 5,522,801 A | 6/1996 | Wang |
| 5,531,788 A | 7/1996 | Dibie et al. |
| 5,545,132 A | 8/1996 | Fagan et al. |
| 5,549,553 A | 8/1996 | Ressemann et al. |
| 5,549,554 A | 8/1996 | Miraki |
| 5,562,620 A | 10/1996 | Klein et al. |
| 5,562,724 A | 10/1996 | Vorwerk et al. |
| 5,562,725 A | 10/1996 | Schmitt et al. |
| 5,562,726 A | 10/1996 | Chuter |
| 5,569,295 A | 10/1996 | Lam |
| 5,571,087 A | 11/1996 | Ressemann et al. |
| 5,575,771 A | 11/1996 | Walinsky |
| 5,575,817 A | 11/1996 | Martin |
| 5,575,818 A | 11/1996 | Pinchuk |
| 5,591,228 A | 1/1997 | Edoga |
| 5,593,442 A | 1/1997 | Klein |
| 5,607,444 A | 3/1997 | Lam |
| 5,609,605 A | 3/1997 | Marshall et al. |
| 5,609,625 A | 3/1997 | Piplani et al. |
| 5,609,627 A | 3/1997 | Goicoechea et al. |
| 5,609,629 A | 3/1997 | Fearnot et al. |
| 5,613,949 A | 3/1997 | Miraki |
| 5,613,980 A | 3/1997 | Chauhan ..................... 606/194 |
| 5,613,981 A | 3/1997 | Boyle et al. |
| 5,617,878 A | 4/1997 | Taheri |
| 5,626,600 A | 5/1997 | Horzewski et al. |
| 5,628,788 A | 5/1997 | Pinchuk |
| 5,632,762 A | 5/1997 | Myler |
| 5,632,763 A | 5/1997 | Glastra |
| 5,632,772 A | 5/1997 | Alcime et al. |
| 5,634,902 A | 6/1997 | Johnson et al. |
| 5,639,278 A | 6/1997 | Dereume et al. |
| 5,643,340 A | 7/1997 | Nunokawa |
| 5,653,743 A | 8/1997 | Martin |
| 5,662,614 A | 9/1997 | Edoga |
| 5,669,924 A | 9/1997 | Shaknovich |
| 5,669,932 A | 9/1997 | Fischell et al. |
| 5,676,696 A | 10/1997 | Morcade |
| 5,676,697 A | 10/1997 | McDonald |
| 5,679,400 A | 10/1997 | Tuch |
| 5,683,451 A | 11/1997 | Lenker et al. |
| 5,690,642 A | 11/1997 | Osborne et al. |
| 5,693,084 A | 12/1997 | Chutter |
| 5,693,086 A | 12/1997 | Goicoechea et al. |
| 5,693,088 A | 12/1997 | Lazarus |
| 5,697,971 A | 12/1997 | Fischell et al. |
| 5,707,354 A | 1/1998 | Salmon |
| 5,709,713 A | 1/1998 | Evan et al. |
| 5,716,365 A | 2/1998 | Goicoechea et al. |
| 5,718,683 A | 2/1998 | Ressemann et al. |

| Patent | Date | Inventor |
|---|---|---|
| 5,718,724 A | 2/1998 | Goicoechea et al. |
| 5,720,735 A | 2/1998 | Dorros |
| 5,723,004 A | 3/1998 | Dereume et al. |
| 5,724,977 A | 3/1998 | Yock et al. |
| 5,728,158 A | 3/1998 | Lau et al. |
| 5,733,303 A | 3/1998 | Israel et al. |
| 5,735,893 A | 4/1998 | Lau et al. |
| 5,746,766 A | 5/1998 | Edoga |
| 5,749,825 A | 5/1998 | Fischell et al. |
| 5,749,848 A | 5/1998 | Jang et al. |
| 5,755,734 A | 5/1998 | Richter et al. |
| 5,755,735 A | 5/1998 | Richter et al. |
| 5,755,770 A | 5/1998 | Ravenscroft |
| 5,755,771 A | 5/1998 | Penn et al. |
| 5,755,778 A | 5/1998 | Kleshinski |
| 5,762,631 A | 6/1998 | Klein |
| 5,776,101 A | 7/1998 | Goy |
| 5,776,161 A | 7/1998 | Globerman |
| 5,776,180 A | 7/1998 | Goicoechea et al. |
| 5,782,906 A | 7/1998 | Marshall et al. |
| 5,800,450 A | 9/1998 | Lary et al. |
| 5,800,508 A | 9/1998 | Goicoechea et al. |
| 5,814,061 A | 9/1998 | Osborne et al. |
| 5,817,126 A | 10/1998 | Imran |
| 5,824,008 A | 10/1998 | Bolduc et al. |
| 5,824,036 A | 10/1998 | Lauterjung |
| 5,824,040 A | 10/1998 | Cox et al. |
| 5,824,041 A | 10/1998 | Lenker et al. |
| 5,824,044 A | 10/1998 | Quiachon et al. |
| 5,827,320 A | 10/1998 | Richter et al. |
| 5,833,650 A | 11/1998 | Imran |
| 5,836,966 A | 11/1998 | St. Germain |
| 5,837,008 A | 11/1998 | Berg et al. |
| 5,843,031 A | 12/1998 | Hermann et al. ............. 604/95 |
| 5,843,160 A | 12/1998 | Rhodes |
| 5,843,164 A | 12/1998 | Frantzen et al. |
| 5,846,204 A | 12/1998 | Solomon |
| 5,851,210 A | 12/1998 | Torossian |
| 5,851,464 A | 12/1998 | Davila et al. |
| 5,855,600 A | 1/1999 | Alt |
| 5,855,601 A | 1/1999 | Bessler et al. |
| 5,865,178 A | 2/1999 | Yock |
| 5,868,777 A | 2/1999 | Lam |
| 5,871,536 A | 2/1999 | Lazarus |
| 5,871,537 A | 2/1999 | Holman et al. |
| 5,891,133 A | 4/1999 | Murphy-Chutorian |
| 5,897,588 A | 4/1999 | Hull et al. |
| 5,906,640 A | 5/1999 | Penn et al. |
| 5,907,893 A | 6/1999 | Zadno-Azizi et al. |
| 5,913,895 A | 6/1999 | Burpee et al. |
| 5,913,897 A | 6/1999 | Corso, Jr. et al. |
| 5,921,958 A | 7/1999 | Ressemann et al. |
| 5,922,020 A | 7/1999 | Klein et al. |
| 5,928,248 A | 7/1999 | Acker |
| 5,938,682 A | 8/1999 | Hojeibane |
| 5,938,696 A | 8/1999 | Goicoechea et al. |
| 5,948,016 A | 9/1999 | Jang |
| 5,951,599 A | 9/1999 | McCrory |
| 5,961,548 A | 10/1999 | Shmulewitz |
| 5,967,986 A | 10/1999 | Cimochowski et al. |
| 5,972,018 A | 10/1999 | Israel et al. |
| 6,007,517 A | 12/1999 | Anderson |
| 6,013,054 A | 1/2000 | Juin Yan |
| 6,013,091 A | 1/2000 | Ley et al. |
| 6,017,324 A | 1/2000 | Tu et al. |
| 6,017,363 A | 1/2000 | Hojeibane |
| 6,024,763 A | 2/2000 | Lenker et al. |
| 6,030,414 A | 2/2000 | Taheri |
| 6,033,434 A | 3/2000 | Borghi |
| 6,033,435 A | 3/2000 | Penn et al. |
| 6,036,682 A | 3/2000 | Lange et al. |
| 6,039,749 A | 3/2000 | Marin et al. |
| 6,042,597 A | 3/2000 | Kveen et al. |
| 6,045,557 A | 4/2000 | White et al. |
| 6,048,361 A | 4/2000 | VanOepen |
| 6,056,775 A | 5/2000 | Borghi et al. |
| 6,059,823 A | 5/2000 | Holman et al. |
| 6,059,824 A | 5/2000 | Taheri |
| 6,066,168 A | 5/2000 | Lau et al. |
| 6,068,655 A | 5/2000 | Sequin et al. |
| 6,071,285 A | 6/2000 | Lashinski et al. |
| 6,086,611 A | 7/2000 | Duffy et al. |
| 6,090,127 A | 7/2000 | Globerman |
| 6,090,128 A | 7/2000 | Douglas |
| 6,096,073 A | 8/2000 | Webster et al. |
| 6,099,497 A | 8/2000 | Adams et al. |
| 6,117,117 A | 9/2000 | Mauch |
| 6,117,156 A | 9/2000 | Richter et al. |
| 6,126,685 A | 10/2000 | Lenker et al. |
| 6,129,738 A | 10/2000 | Lashinski et al. |
| 6,129,754 A | 10/2000 | Kanesaka et al. |
| 6,142,973 A | 11/2000 | Carleton et al. |
| 6,152,945 A | 11/2000 | Bachinski et al. |
| 6,165,195 A | 12/2000 | Wilson et al. |
| 6,165,197 A | 12/2000 | Yock |
| 6,165,214 A | 12/2000 | Lazarus |
| 6,179,867 B1 | 1/2001 | Cox |
| 6,183,506 B1 | 2/2001 | Penn et al. |
| 6,183,509 B1 | 2/2001 | Dibie |
| 6,190,403 B1 | 2/2001 | Fischell et al. |
| 6,193,746 B1 | 2/2001 | Strecker |
| 6,203,569 B1 | 3/2001 | Wijay |
| 6,210,380 B1 | 4/2001 | Mauch |
| 6,210,429 B1 | 4/2001 | Vardi |
| 6,217,527 B1 | 4/2001 | Selmon et al. |
| 6,217,608 B1 | 4/2001 | Penn et al. |
| 6,221,080 B1 | 4/2001 | Power |
| 6,221,090 B1 | 4/2001 | Wilson |
| 6,221,098 B1 | 4/2001 | Wilson et al. |
| 6,231,563 B1 | 5/2001 | White et al. |
| 6,231,598 B1 | 5/2001 | Berry et al. |
| 6,231,600 B1 | 5/2001 | Zhong |
| 6,235,051 B1 | 5/2001 | Murphy |
| 6,241,762 B1 | 6/2001 | Shanley |
| 6,258,073 B1 | 7/2001 | Mauch |
| 6,258,099 B1 | 7/2001 | Mareiro et al. |
| 6,258,116 B1 | 7/2001 | Hojeibane |
| 6,258,121 B1 | 7/2001 | Yang et al. |
| 6,261,273 B1 | 7/2001 | Ruiz |
| 6,261,305 B1 | 7/2001 | Marotta et al. |
| 6,261,319 B1 | 7/2001 | Kveen et al. |
| 6,264,682 B1 | 7/2001 | Wilson et al. |
| 6,273,911 B1 | 8/2001 | Cox et al. |
| 6,273,913 B1 | 8/2001 | Wright et al. |
| 6,287,314 B1 | 9/2001 | Lee et al. |
| 6,290,673 B1 | 9/2001 | Shanley |
| 6,293,967 B1 | 9/2001 | Shanley |
| 6,299,634 B1 | 10/2001 | Bergeron |
| 6,302,906 B1 | 10/2001 | Goicoechea et al. |
| 6,309,412 B1 | 10/2001 | Lau et al. |
| 6,309,414 B1 | 10/2001 | Rolando et al. |
| 6,312,459 B1 | 11/2001 | Huang et al. |
| 6,325,821 B1 | 12/2001 | Gaschino et al. |
| 6,325,826 B1 | 12/2001 | Vardi et al. |
| 6,334,870 B1 | 1/2002 | Her et al. |
| 6,346,089 B1 | 2/2002 | Dibie |
| 6,350,278 B1 | 2/2002 | Lenker et al. |
| 6,355,060 B1 | 3/2002 | Lenker et al. |
| 6,361,544 B1 | 3/2002 | Wilson et al. |
| 6,361,555 B1 | 3/2002 | Wilson |
| 6,383,215 B1 | 5/2002 | Sass |
| 6,387,120 B2 | 5/2002 | Wilson et al. |

| | | | | | | |
|---|---|---|---|---|---|---|
| 6,395,018 B1 | 5/2002 | Castaneda | | 2003/0014102 A1 | 1/2003 | Hong et al. |
| 6,398,792 B1 | 6/2002 | O'Connor | | 2003/0023301 A1 | 1/2003 | Cox et al. |
| 6,398,804 B1 | 6/2002 | Spielberg | | 2003/0050688 A1 | 3/2003 | Fischell et al. |
| 6,428,570 B1 | 8/2002 | Globerman | | 2003/0074047 A1 | 4/2003 | Richter |
| 6,432,133 B1 | 8/2002 | Lau et al. | | 2003/0093109 A1 | 5/2003 | Mauch |
| 6,436,104 B2 | 8/2002 | Hojeibane | | 2003/0114912 A1 | 6/2003 | Sequin et al. |
| 6,436,134 B2 | 8/2002 | Richter et al. | | 2003/0114915 A1 | 6/2003 | Mareiro et al. |
| 6,478,816 B1 | 11/2002 | Kveen et al. | | 2003/0125791 A1 | 7/2003 | Sequin et al. |
| 6,482,211 B1 | 11/2002 | Choi | | 2003/0125799 A1 | 7/2003 | Limon et al. |
| 6,485,511 B2 | 11/2002 | Lau et al. | | 2003/0125802 A1 | 7/2003 | Callol et al. |
| 6,494,905 B1 | 12/2002 | Zedler et al. | | 2004/0015227 A1 | 1/2004 | Vardi et al. |
| 6,511,504 B1 | 1/2003 | Lau et al. | | 2004/0049259 A1 | 3/2004 | Strecker |
| 6,511,505 B2 | 1/2003 | Cox et al. | | 2004/0072849 A1 | 4/2004 | Schreiber et al. |
| 6,520,988 B1 | 2/2003 | Colombo et al. | | 2004/0133268 A1 | 7/2004 | Davidson et al. |
| 6,527,799 B2 | 3/2003 | Shanley | | 2004/0138737 A1 | 7/2004 | Davidson et al. |
| 6,540,719 B2 | 4/2003 | Bigus et al. | | 2004/0148006 A1 | 7/2004 | Davidson et al. |
| 6,540,779 B2 | 4/2003 | Richter et al. | | | | |
| 6,572,647 B1 | 6/2003 | Supper | | FOREIGN PATENT DOCUMENTS | | |
| 6,579,309 B1 | 6/2003 | Loos et al. | | DE | 29701758 | 7/1997 |
| 6,579,312 B2 | 6/2003 | Wilson et al. | | EP | 551179 | 7/1993 |
| 6,582,394 B1 | 6/2003 | Reiss et al. | | EP | 684022 | 11/1995 |
| 6,582,459 B1 | 6/2003 | Lau et al. | | EP | 804907 | 5/1997 |
| 6,596,022 B2 | 7/2003 | Lau et al. | | EP | 876805 | 11/1998 |
| 6,599,316 B2 | 7/2003 | Vardi et al. | | EP | 884028 | 12/1998 |
| 6,645,241 B1 | 11/2003 | Strecker | | EP | 891751 | 1/1999 |
| 6,689,156 B1 | 2/2004 | Davidson et al. | | EP | 897698 | 2/1999 |
| 6,692,483 B2 | 2/2004 | Vardi et al. | | EP | 897700 | 2/1999 |
| 6,706,062 B2 | 3/2004 | Vardi et al. | | EP | 904745 | 3/1999 |
| 2001/0012927 A1 | 8/2001 | Mauch | | EP | 1031328 | 8/2000 |
| 2001/0016767 A1 | 8/2001 | Wilson et al. | | EP | 1031330 | 8/2000 |
| 2001/0016768 A1 | 8/2001 | Wilson et al. | | EP | 1157674 | 11/2001 |
| 2001/0027291 A1 | 10/2001 | Shanley | | EP | 646365 | 1/2004 |
| 2001/0027338 A1 | 10/2001 | Greenberg | | FR | 2678508 | 7/1991 |
| 2001/0029396 A1 | 10/2001 | Wilson et al. | | FR | 2678508 | 1/1993 |
| 2001/0037116 A1 | 11/2001 | Wilson et al. | | WO | WO 88/06026 | 2/1988 |
| 2001/0037138 A1 | 11/2001 | Wilson et al. | | WO | WO 88/06026 | 8/1988 |
| 2001/0037146 A1 | 11/2001 | Lau et al. | | WO | WO 90/13332 | 11/1990 |
| 2001/0037147 A1 | 11/2001 | Lau et al. | | WO | WO 91/12779 | 9/1991 |
| 2001/0039395 A1 | 11/2001 | Mareiro et al. | | WO | WO 92/19308 | 11/1992 |
| 2001/0039448 A1 | 11/2001 | Dibie | | WO | WO 95/08965 | 4/1995 |
| 2001/0047201 A1 | 11/2001 | Cox et al. | | WO | WO 95/21592 | 8/1995 |
| 2001/0049552 A1 | 12/2001 | Richter et al. | | WO | WO 96/41592 | 6/1996 |
| 2001/0056297 A1 | 12/2001 | Hojeibane | | WO | WO 96/29955 | 10/1996 |
| 2002/0013618 A1 | 1/2002 | Marotta et al. | | WO | WO 96/41592 | 12/1996 |
| 2002/0013619 A1 | 1/2002 | Shanley | | WO | WO 97/09946 | 3/1997 |
| 2002/0022874 A1 | 2/2002 | Wilson | | WO | WO 97/33532 | 3/1997 |
| 2002/0026232 A1 | 2/2002 | Marotta et al. | | WO | WO 97/16217 | 5/1997 |
| 2002/0032478 A1 | 3/2002 | Bockstegers et al. | | WO | WO 97/45073 | 5/1997 |
| 2002/0035392 A1 | 3/2002 | Wilson | | WO | WO 97/26936 | 7/1997 |
| 2002/0042650 A1 | 4/2002 | Vardi et al. | | WO | WO 97/32544 | 9/1997 |
| 2002/0052648 A1 | 5/2002 | McGuckin et al. | | WO | WO 97/33532 | 9/1997 |
| 2002/0058990 A1 | 5/2002 | Jang | | WO | WO 97/41803 | 11/1997 |
| 2002/0072790 A1 | 6/2002 | McGuckin et al. | | WO | WO 97/45073 | 12/1997 |
| 2002/0107564 A1 | 8/2002 | Cox et al. | | WO | WO 98/17204 | 4/1998 |
| 2002/0111675 A1 | 8/2002 | Wilson | | WO | WO 98/19628 | 5/1998 |
| 2002/0123790 A1 | 9/2002 | White et al. | | WO | WO 98/35634 | 8/1998 |
| 2002/0123797 A1 | 9/2002 | Majercak | | WO | WO 98/36709 | 8/1998 |
| 2002/0123798 A1 | 9/2002 | Burgermeister | | WO | WO 98/37833 | 9/1998 |
| 2002/0151959 A1 | 10/2002 | Von Oepen | | WO | WO 98/44871 | 10/1998 |
| 2002/0156516 A1 | 10/2002 | Vardi et al. | | WO | WO 98/48733 | 11/1998 |
| 2002/0156517 A1 | 10/2002 | Perouse | | WO | WO 98/52497 | 11/1998 |
| 2002/0165604 A1 | 11/2002 | Shanley | | WO | WO 99/15103 | 4/1999 |
| 2002/0173835 A1 | 11/2002 | Bourang et al. | | WO | WO 99/17680 | 4/1999 |
| 2002/0173840 A1 | 11/2002 | Brucker et al. | | WO | WO 99/34749 | 7/1999 |
| 2002/0177892 A1 | 11/2002 | Globerman | | WO | WO 99/36072 | 7/1999 |
| 2002/0183763 A1 | 12/2002 | Callol et al. | | WO | WO 99/39661 | 8/1999 |
| 2002/0193872 A1 | 12/2002 | Trout et al. | | WO | WO 99/58059 | 11/1999 |
| 2002/0193873 A1 | 12/2002 | Brucker et al. | | WO | WO 99/65419 | 12/1999 |
| 2003/0004535 A1 | 1/2003 | Musbach et al. | | WO | WO 00/00104 | 1/2000 |
| 2003/0009209 A1 | 1/2003 | Hojeibane | | WO | WO 00/12166 | 3/2000 |
| 2003/0009214 A1 | 1/2003 | Shanley | | WO | WO 00/13613 | 3/2000 |

| | | |
|---|---|---|
| WO | WO 00/53122 | 9/2000 |
| WO | WO 00/74595 | 12/2000 |
| WO | WO 01/21095 | 3/2001 |
| WO | WO 01/21109 | 3/2001 |
| WO | WO 01/21244 | 3/2001 |
| WO | WO 01/70299 | 9/2001 |
| WO | WO 02/68012 | 9/2002 |
| WO | WO 02/76333 | 10/2002 |
| WO | WO 02/94336 | 11/2002 |
| WO | WO 03/55414 | 7/2003 |

OTHER PUBLICATIONS

Nakamura et al., "Techniques for Palmaz–Schatz Stent Deployment in Lesions with a Large Side Branch" Catheterization & Cardiovascular Diagnosis, (1995) 34:353–361.

Serruys et al., "A Comparison of Balloon–Expandable–Stent Implantation with Balloon Angioplasty in Patients with Coronary Artery Disease" The New England Journal of Medicine, (1994) 331(8): 489–495.

Colombo et al., "Kissing Stents for Bifurcational Coronary Lesion" Catheterization and Cardiovascular Diagnosis, (1993) 30:327–330.

Carrie et al., "T–Shaped Stent Placement: A Technique for the Treatment of Dissected Bifurcation Lesions" Catheterization and Cardiovascular Diagnosis, (1996) 37:311–313.

Katoh et al., "New Double Wire Technique to Stent Ostial Lesions" Catheterization and Cardiovascular Diagnosis, (1997) 40:400–402.

Serruys et al., *The New England Journal of Medicine*, vol. 331, No. 8, pp. 489–495 (1994).

Fischmann et al., *The New England Journal of Medicine*, vol. 331, No. 8, pp. 496–501 (1994).

Nakamura et al., *Catheterization & Cardiovascular Diagnosis* 34–353–361 (1995).

Caputo et al., *The American Journal of Cardiology*, vol. 7, pp. 1226–1230 (1996).

Colombo et al., *Catheterization and Cardiovascular Diagnosis*, vol. 30, pp. 327–330 (1993).

Carrie et al., *Catheterization and Cardiovascular Diagnosis*, vol. 37, pp. 311–313 (1996).

Katoh et al., *Catheterization and Cardiovascular Diagnosis*, vol. 40, pp. 400–402 (1997).

Lewis et al., *American Heart Journal*, vol. 127, pp. 1600–1607 (1994).

Dichek, D.A. et al.; *Circulation*, 80: 1347–1353 (1989).

Chevalier, B. et al.; *American Journal of Cardiology*, 82: 943–949 (1998).

Yamashita, T. et al.; *Journal of American College of Cardiology*, 35: 1145–1151 (2000).

Satler, S., et al.; *Catheterization and Cardiovascular Interventions*, 50: 411–412 (2000).

BIFURCATION LESION STENT DELIVERY USING MULTIPLE GUIDEWIRES

CROSS REFERENCE TO RELATED APPLICATIONS

This application is a continuation in part application of U.S. patent application Ser. No. 09/663,111, filed Sep. 15, 2000, which is a continuation in part application of U.S. patent application Ser. No. 09/614,472, filed Jul. 11, 2000, now abandoned, which is a continuation in part application of U.S. patent application Ser. No. 09/325,996, filed Jun. 4, 1999, now abandoned, and Ser. No. 09/455,299, filed Dec. 6, 1999, now U.S. Pat. No. 6,692,483, the complete disclosures of which are herein incorporated by reference.

BACKGROUND OF THE INVENTION

This invention relates generally to the field of medical stents. More specifically, the invention relates to techniques for deploying stents into vessels such that a side opening in the stent wall is aligned with an ostium of a branch vessel.

A type of endoprosthesis device, commonly referred to as a stent, may be placed or implanted within a vein, artery or other tubular body organ for treating occlusions, stenoses, or aneurysms of a vessel by reinforcing the wall of the vessel or by expanding the vessel. Stents have been used to treat dissections in blood vessel walls caused by balloon angioplasty of the coronary arteries as well as peripheral arteries and to improve angioplasty results by preventing elastic recoil and remodeling of the vessel wall. Two randomized multicenter trials have shown a lower restenosis rate in stent treated coronary arteries compared with balloon angioplasty alone (Serruys, P W et al., *New England Journal of Medicine* 331:489–495 (1994) and Fischman, D L et al. *New England Journal of Medicine* 331:496–501 (1994), the disclosures of which are herein incorporated by reference. Additionally, regular stents have been used at bifurcation lesions with limited success rates (Chevalier, B. et al. *American Journal of Cardiology* 82:943–949 (1998), Yamashita T. et al. *Journal of American College of Cardiology* 35:1145–1151 (2000) and Satler S. et al. *Catheterization and Cardiovascular Interventions* 50:411–412 (2000). Side branch jailing, fear of plaque shifting and total occlusion and difficulty of the procedure require novel, easier to use, special stents to be developed. Stents have been successfully implanted in the urinary tract, the bile duct, the esophagus and the tracheo-bronchial tree to reinforce those body organs, as well as implanted into the neurovascular, peripheral vascular, coronary, cardiac, and renal systems, among others. The term "stent" as used in this Application is a device that is intraluminally implanted within bodily vessels to reinforce collapsing, dissected, partially occluded, weakened, diseased or abnormally dilated or small segments of a vessel wall.

One of the drawbacks of conventional stents is that they are generally produced in a straight tubular configuration. The use of such stents to treat diseased vessels at or near a bifurcation (branch point) of a vessel may create a risk of compromising the degree of patency of the main vessel and/or its branches, or the bifurcation point and also limits the ability to insert a branch stent into the side branch if the result of treatment of the main, or main, vessel is suboptimal. Suboptimal results may occur as a result of several mechanisms, such as displacing diseased tissue, plaque shifting, snow plowing, chronic total occlusion, vessel spasm, dissection with or without intimal flaps, thrombosis, and embolism.

As described in related U.S. patent application Ser. No. 08/744,002 filed Nov. 4, 1996 (now abandoned), Ser. No. 09/007,265 filed Jan. 14, 1998, Ser. No. 08/935,383, filed Sep. 23, 1997, 60/088,301 filed Jun. 5, 1998, and Ser. No. 09/663,111, filed Sep. 15, 2000, and PCT Patent Application Publication No. WO 99/00835 filed Jan. 14, 1998, systems and methods have been developed for deploying a main stent in a main vessel at the intersection of a main vessel and a branch vessel. Further, a branch stent may be positioned within a branch vessel through a side opening in the main stent. The complete disclosures of all these references are herein incorporated by reference.

This invention relates to other novel techniques for deploying stents at such vessel intersections to permit the side opening to be aligned with the ostium of the branch vessel. Some embodiments are particularly directed toward managing the guidewires used to introduce the catheter systems to the region of interest.

SUMMARY OF THE INVENTION

The invention provides systems and methods for deploying a main vessel stent in a main vessel, with a side hole in the main stent being in registry with the ostium of a branch vessel. A variety of catheter designs may be employed to deploy and position the main and branch vessel stents. Such catheters may be used in connection with multiple guidewires that terminate in the main and branch vessels. These guidewires may be used to facilitate introduction of the catheter, any stents, and/or to properly orient the stent within the vessel.

In one particular embodiment, the methods of the invention may utilize a catheter system comprising a catheter body having a main vessel guidewire lumen and a side member that is operably coupled to the catheter body. The side member has a branch vessel guidewire lumen. The catheter body further includes a balloon, and the stent is disposed over the balloon. The side member extends into the stent and exits the stent through the side hole of the stent.

According to one method, a main vessel guidewire is inserted into the main vessel until a distal end of the main vessel guidewire passes beyond the ostium of the branch vessel, and a branch vessel guidewire is inserted into the vessel until a distal end of the branch vessel guidewire passes into the branch vessel. The catheter system is then advanced over the main and branch vessel guidewires, with the main and branch vessel guidewires passing through the main vessel guidewire and the branch vessel guidewire lumens of the catheter body, respectively.

In the event the guidewires cross, preventing further advancement of the catheter system, the branch vessel guidewire may be withdrawn into the side member to uncross the guidewires. Once uncrossed, the branch vessel guidewire is re-advanced into the branch vessel. At this point, the catheter system may be further advanced over the guidewires until the catheter body passes beyond the ostium of the branch vessel and the side member extends into the branch vessel. The balloon may then be inflated to deploy the stent within the main vessel, with the side hole of the stent being aligned with the ostium. Alternatively, a backup main vessel guidewire may be introduced into the main vessel, and the main vessel guidewire may be withdrawn into the catheter body to uncross the wires.

Optionally, a backup guidewire may be introduced into the branch vessel prior to withdrawing the branch vessel guidewire into the side member. The backup guidewire may then be withdrawn from the branch vessel prior to deploying the stent. Similarly, a backup main vessel guidewire may be introduced into the main vessel prior to withdrawing the main vessel guidewire into the catheter body. The backup main vessel guidewire may then be withdrawn from the main vessel prior to deploying the stent.

In one particular aspect, the catheter body may include at least one radiopaque marker and the side member may also include at least one radiopaque marker. With such a configuration, separation of the markers may be conveniently observed using fluoroscopy to indicate that the catheter body has passed beyond the ostium and the side member has passed into the branch vessel, causing the side hole of the stent to be aligned with the ostium of the branch vessel.

In an alternative method a main vessel guidewire is inserted into the main vessel until a distal end of the main vessel guidewire passes beyond the ostium. A backup branch vessel guidewire is inserted into the main vessel until a distal end of the backup branch vessel guidewire passes into the branch vessel. The catheter system is then advanced over the main vessel guidewire until reaching the distal end of the guiding catheter, with the backup branch vessel guidewire extending alongside the catheter system. A branch vessel guidewire is inserted through the branch vessel guidewire lumen of the side member of the catheter system until a distal end of the branch vessel guidewire passes into the branch vessel. The catheter system is then advanced over the main vessel guidewire and the branch vessel guidewire until the catheter body extends beyond the ostium and the side member extends into the branch vessel.

Once the stent is in position, the backup branch vessel guidewire is withdrawn from the branch vessel and the balloon may be inflated to deploy the stent within the main vessel, with the side hole being aligned with the ostium. Optionally, a branch vessel stent may also be placed within the branch vessel.

DESCRIPTION OF THE SPECIFIC EMBODIMENTS

The present invention provides systems and methods for deploying stents at a vessel bifurcation such that a specifically designed cell to function as a branch aperture referred to as a side hole of the stent throughout this Application, in the stent is in registry with the ostium of the branch vessel. In one aspect, various techniques are provided for managing the guidewires over which the stents and stent delivery catheters are directed. More specifically, the invention provides techniques to help prevent the crossing of guidewires or simply uncross them when introducing catheters used to deploy stents or other devices that require advancement over multiple guidewires, where it is important for the guidewires to be tangle free and parallel with respect to each other. In this way, the catheters may more easily be introduced to the diseased region. More specifically, the distal end of the bifurcation stent delivery catheter and its side member may freely rotate so the side hole of the stent properly faces the ostium of the branch.

Applications of the invention include the cardiac, coronary, renal, peripheral vascular, gastrointestinal, pulmonary, urinary and neurovascular systems and the brain. Advantages of the invention include, but are not limited to, the use of an improved stent delivery apparatus, which may deliver stents to: 1) completely cover the bifurcation point of bifurcation vessels; 2) be used to treat lesions in one branch of a bifurcation while preserving access to the other branch for future treatment; 3) allow for differential sizing of the stents in a bifurcated stent apparatus even after a main stent is implanted; 4) treat bifurcation lesions in a bifurcated vessel where the branch vessel extends from the side of the main vessel; and 5) be marked with, or at least partly constructed of, material which is imageable by commonly used intraluminal catheterization visualization techniques including but not limited to ultrasound or x-ray.

As described herein, a side hole in the main vessel stent refers to specific cell of the stent, which form a relatively large opening and which is intended to be aligned with the ostium of the branch vessel. Such a side hole is separate from any of the multiple passageways extending through the side of the stent between struts in the stent geometry. Accordingly, the side hole in the stent is a hole, which is understood to be larger than other passages through the stent, except the longitudinal bore of the stent itself. Additionally the side hole of the stent is configured such that a central axis extending perpendicularly through the side hole is generally perpendicular to the longitudinal axis of the stent. In some aspects, this side hole is defined by a band of continuous material, which outlines the perimeter of the side hole. This continuous band of material preferably comprises serpentine patterns over its length so that the area of the side hole expands together with the expansion of the stent. In various aspects, the continuous band comprises protrusions, which project inwardly from a peripheral edge of the side opening and, when expanded, deflect perpendicularly to the longitudinal axis of the stent. Preferably, these protrusions (or expandable portions) are initially aligned within a cylindrical envelope of the tubular body of the stent.

Figure 1:
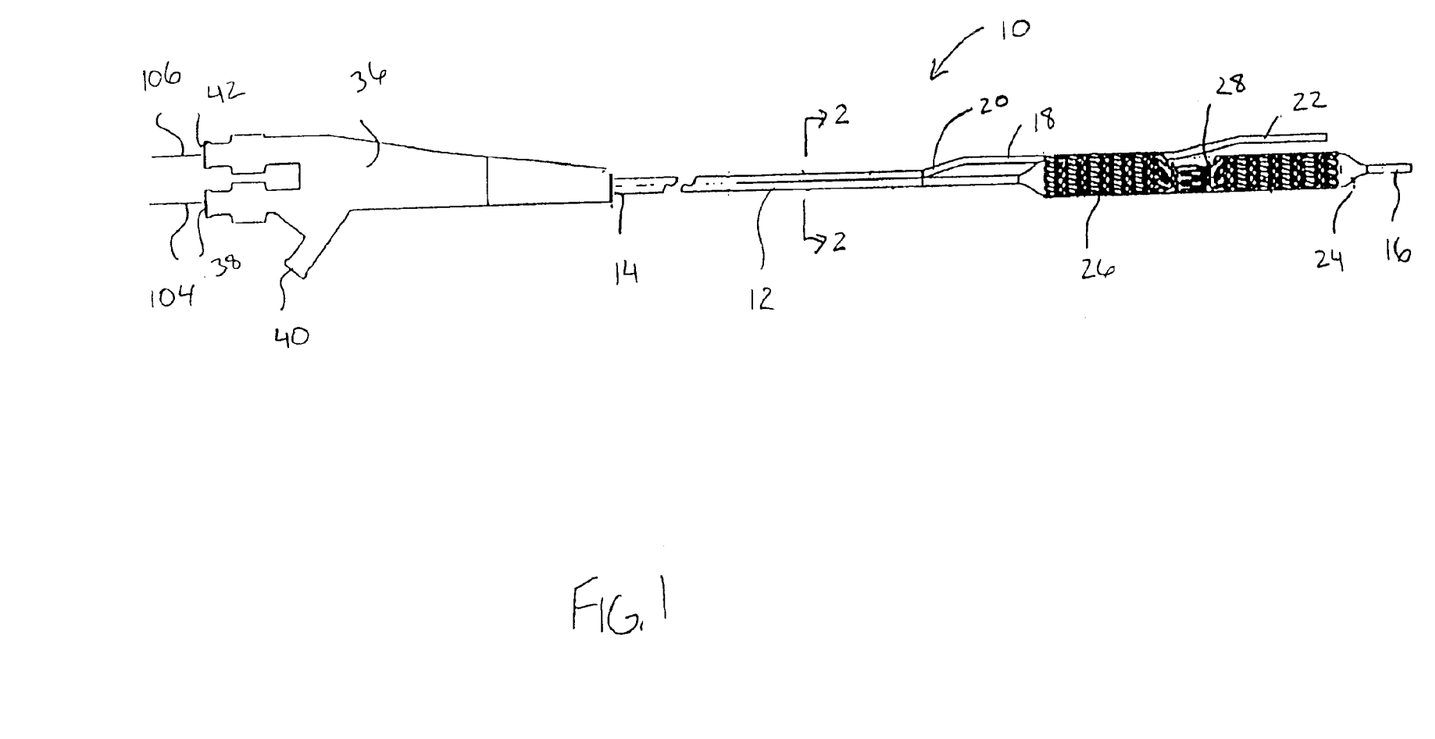
FIG. 1 is a side view of an embodiment of a catheter having a stent that may be deployed within a vessel such that a side hole of the stent is in registry with an ostium of a branch vessel.

Referring now to FIG. 1, one embodiment of a stent delivery catheter 10 will be described. Catheter 10 may be constructed similar to that described in U.S. patent application Ser. No. 09/663,111, previously incorporated by reference. Catheter 10 comprises a dual lumen catheter body 12 having a proximal end 14 and a distal end 16. Attached to catheter body 12 is a side member 18 having a proximal end 20 and a distal end 22. As shown in FIG. 1, distal end 22 of side member 18 is detached from distal end 16 of catheter body 12. The length of side member 18 that is detached from catheter body 12 may be in the range from about 2 cm to about 10 cm. Such a configuration is advantageous in that it permits rotation of distal end 16, side member 18 and stent 26 of catheter 10, thereby allowing side hole 28 of stent 26 to correctly orient itself without requiring rotation of the main shaft from the proximal end. In this way, the clinician may easily align the side hole of the main stent with the ostium of the branch vessel without having to rotate the proximal end of catheter 10.

Disposed at distal end 16 is a balloon 24 over which a main vessel stent 26 having a side hole 28 is crimped. Distal end 22 of side member 18 passes between main vessel stent 26 and balloon 24 and exits stent 26 through side hole 28. In this way, distal end 22 may be positioned within a branch vessel stent in a manner similar to that previously described with other embodiments.

Figure 2:
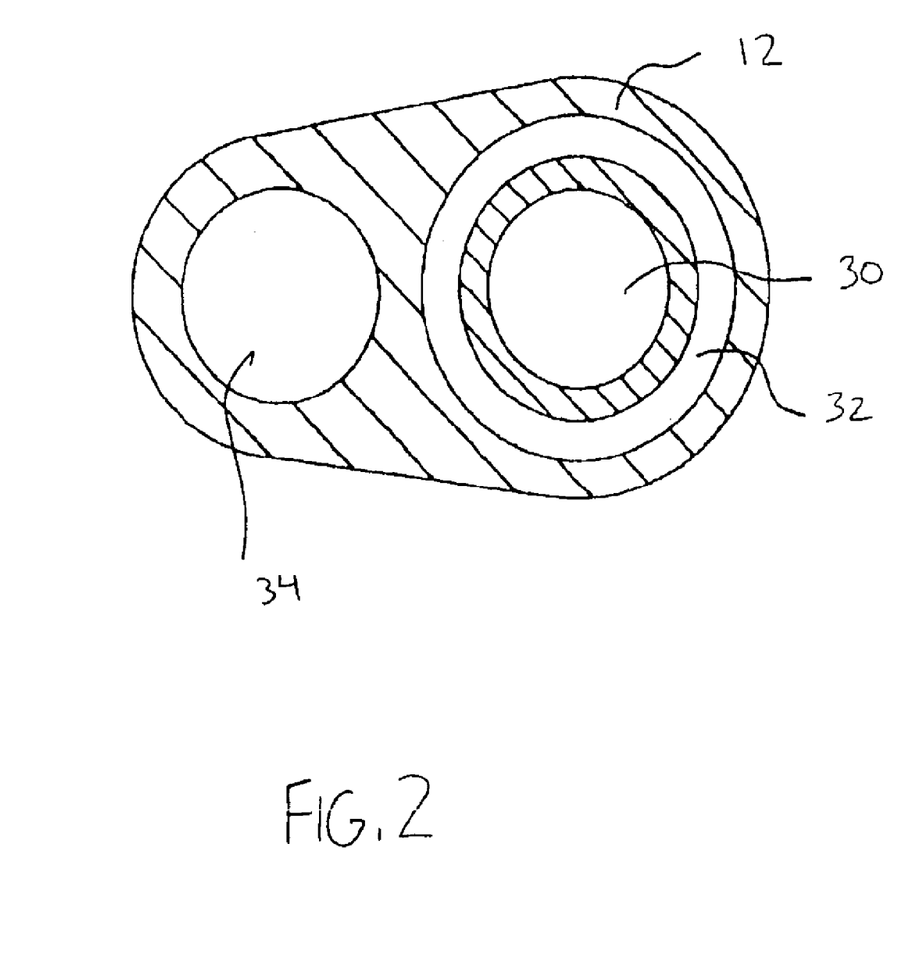
FIG. 2 is a cross sectional view of the catheter of FIG. 1, taken along lines 2—2.

As shown in FIG. 2, passing through dual lumen catheter body 12 is a main vessel guidewire lumen 30 and a balloon inflation lumen 32 that is disposed about main vessel guidewire lumen 30. Passing through side member 18 and passing through dual lumen catheter body 12 is a branch vessel guidewire lumen 34. In this way, catheter 10 may be advanced over main and branch vessel guidewires in a manner similar to that previously described with other embodiments. Further, balloon 24 may be inflated using balloon inflation port 40 (see FIG. 3) and balloon inflation lumen 32.

Figure 3:
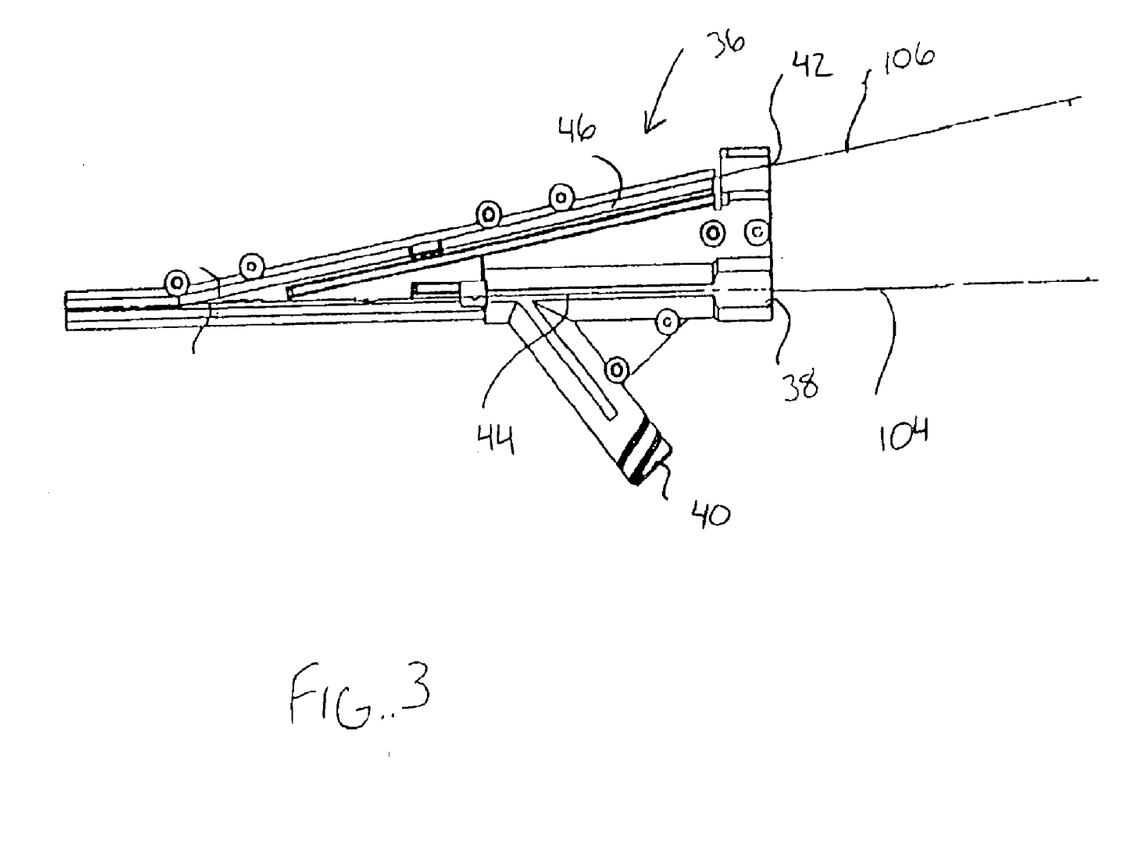
FIG. 3 is a more detailed view of a proximal hub of the catheter of FIG. 1.

As best shown in FIGS. 1 and 3, a proximal hub 36 is coupled to proximal end 14 of catheter 10. Hub 36 further includes a main vessel guidewire port 38, a balloon inflation port 40 and a branch vessel guidewire port 42. Balloon inflation port 40 is in fluid communication with balloon inflation lumen 32 (see FIG. 2) to permit balloon 24 to be inflated and deflated using an inflation device, such as a syringe or an indeflator that is coupled to port 40. Main vessel guidewire port 38 leads to a main vessel guidewire channel 44, and branch vessel guidewire port 42 leads to a branch vessel guidewire channel 46. In this way, a main vessel guidewire 104 may be passed through port 38, through channel 44 and into guidewire lumen 30 (see FIG. 2). In a similar manner, a branch vessel guidewire 106 may be passed through port 42, through channel 46 and into lumen 34 (see FIG. 2).

Channels 44 and 46 are angled relative to each other, preferably at an angle in the range from about 0 to 20 degrees, and more preferably about 10 to about 20 degrees. By configuring channels 44 and 46 in this manner excessive friction may be avoided when positioning or moving the guidewires within catheter 10. In this way, catheter 10 may more easily be advanced over both guidewires 104 and 106 at the same time. Further, the guidewires are held sufficiently close to permit an operator to simultaneously grasp and hold onto both guidewires with one hand while advancing or withdrawing catheter 10 over the two guidewires with the other hand. In addition, the guidewire ports 38 and 42 are held sufficiently far apart to permit a syringe to be coupled to ports 38 and 42, or to permit separate luer fittings to cover ports 38 and 42.

Figure 4:
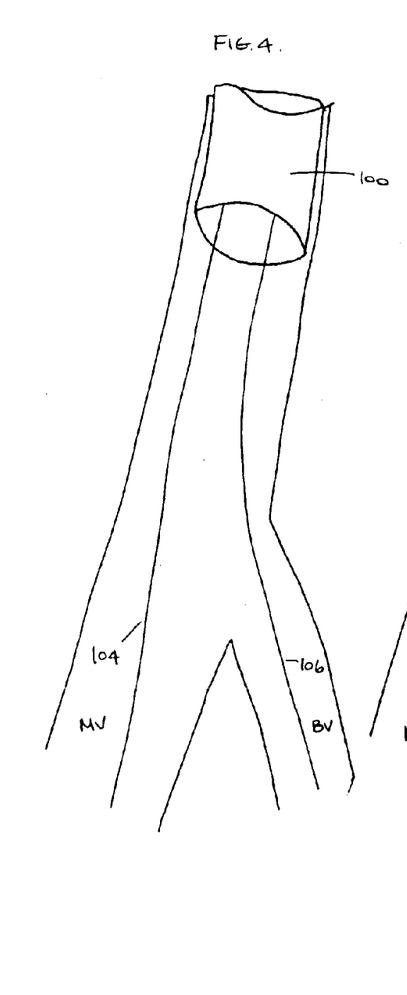
FIG. 4 illustrates the introduction of a main vessel guidewire and a branch vessel guidewire through a guiding catheter.

Referring now to FIGS. 4–8, one method for utilizing catheter 10 to deploy stent 26 within a vessel will be described. As shown in FIG. 4, a guiding catheter 100 is initially introduced into the patient through the femoral, radial or any other suitable artery as is known in the art. For convenience of illustration, the diseased sections of main vessel MV and branch vessel BV have been omitted from the figures. With guiding catheter 100 in place, a main vessel guidewire 104 is advanced through guiding catheter 100 and into main vessel MV until guidewire 104 extends past the ostium of branch vessel BV. Typically, main vessel guidewire 104 will be advanced past the diseased region in main vessel MV. A branch vessel guidewire 106 is also routed through guiding catheter 100, through main vessel MV and into branch vessel BV. In some cases, branch vessel BV may also include a diseased region that is to be treated. In that case, branch vessel guidewire 106 will be advanced past the diseased region in branch vessel BV.

With main vessel guidewire 104 and branch vessel guidewire 106 in place, the physician may optionally perform pre-treatment methods to prepare the site for subsequent stent implantation, including techniques such as debulking and "kissing balloon technique" to predialate both vessels to help prevent plaque shift. Such techniques sometimes involve advancing two balloons over guidewires 104 and 106. The balloons are positioned such that when inflated their proximal edges touch or "kiss" each other to prevent plaque shift into one or the other vessel. In other words, main vessel MV and branch vessel BV are exposed to balloon pressures at the same time, and the plaque is compressed without causing it to shift to block the other vessel, an event known in the art as "snowplowing." After the pre-treatment of the arteries, both balloons are withdrawn but main vessel guidewire 104 and branch vessel guidewire 106 are left in place.

Catheter 10 is then loaded onto guidewires 104 and 106, outside of the patient's body. Main vessel guidewire 104 is inserted through main vessel guidewire lumen 30 (see. FIG. 2) and branch vessel guidewire 106 is routed through branch vessel guidewire lumen 34 (see FIG. 2). In this way, main vessel guidewire 104 passes through catheter body 12 and extends into main vessel MV, and branch vessel guidewire 106 extends through side member 18 and out of distal end 22 of side member 18 and extends into branch vessel BV. Hence, as catheter 10 is advanced through guiding catheter 100, guidewires 104 and 106 pass through separate guidewire lumens to prevent wire crossing within the catheter.

Figure 5:
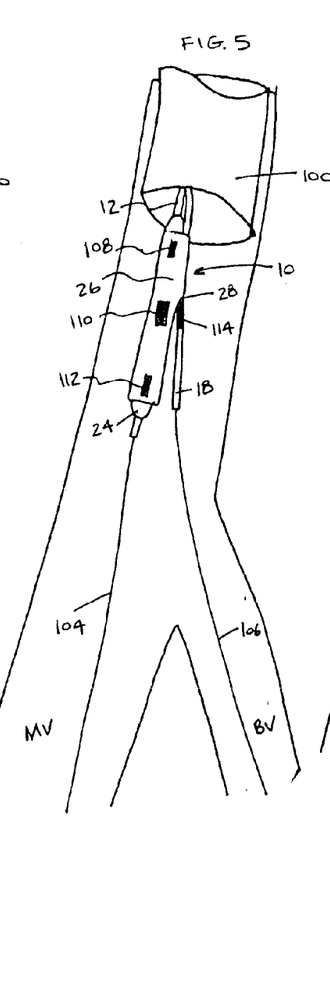
FIG. 5 illustrates the introduction of the catheter of FIG. 1 over the guidewires of FIG. 4.

As catheter 10 is advanced through the body, fluoroscopically visibly markers on catheter 10 may be observed using standard angiographic imaging, performed at various projections. For example, as shown in FIG. 5, three such markers 108, 110 and 112 are disposed within balloon 24. For convenience of illustration, markers 108, 110 and 112 located within balloon 24 are shown in solid lines. Another marker 114 is disposed on side member 18. Prior to reaching the vessel bifurcation, side member 18 remains close and parallel to the longitudinal axis of stent 26. As such, markers 108, 110, and 112, which correspond to proximal, middle and distal portions of stent 26 may be easily observed by angiography. Marker 114 on side member 18 overlaps marker 110 within balloon 24, giving the appearance that there is one marker near the center of stent 26. This indicates that side member 18 has not yet diverged from stent 26 and thus catheter 10 is not yet at the bifurcation point. Obtaining angiographic views of the bifurcation point at various projection angles confirms divergence of the markers and thus side member 18.

Figure 6:
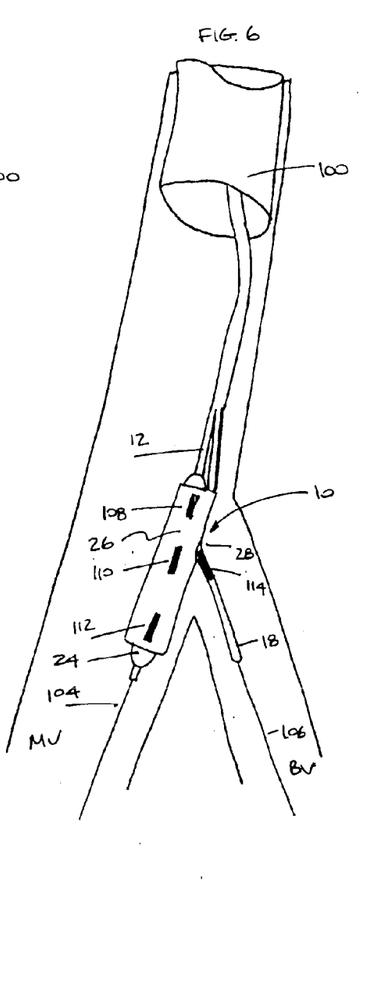
FIG. 6 illustrates the advancement of the catheter of FIG. 1 over the guidewires of FIG. 4 to position the stent at the vessel bifurcation and the separation of side member.

As shown in FIG. 6, catheter 10 is then advanced into the area of bifurcation such that side member 18 passes into branch vessel BV and distal end of catheter body 12 passes beyond the vessel bifurcation and further into main vessel MV. This fact may be observed fluoroscopically by noting that marker 114 on side member 18 separates from middle marker 110 within balloon 24. The physician may take angiographic images from various angles to ensure that such marker separation has indeed occurred. Beyond observing the marker separation, advancing catheter 10 too far will result in a feeling of resistance. This is due to side member 18 reaching the crotch of the bifurcation and not having anywhere else to proceed.

Figure 7:
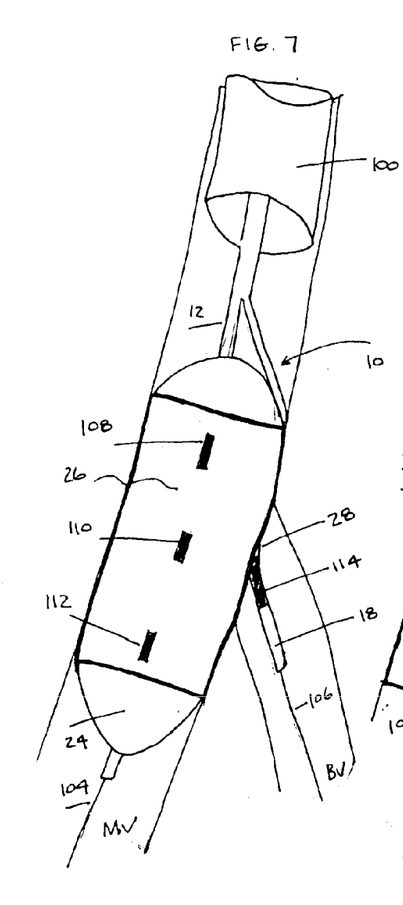
FIG. 7 illustrates inflation of the balloon located at the distal end of the catheter of FIG. 1 to deploy the stent.
Figure 8:
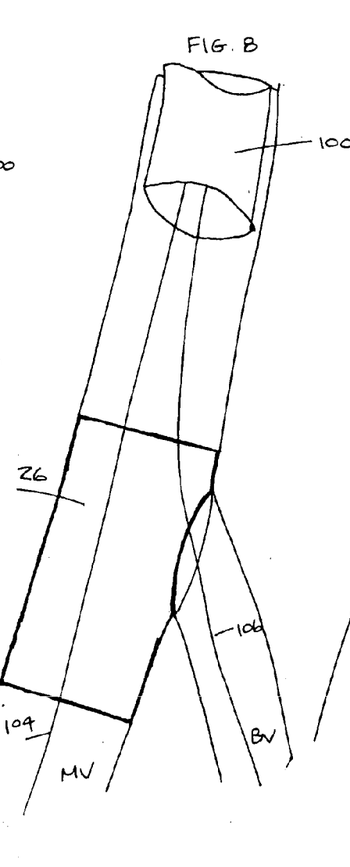
FIG. 8 illustrates the stent of FIG. 7 after deployment and with the catheter system removed from the main vessel.

When such marker separation has occurred, stent 26 is properly aligned with the ostium of branch vessel BV. Balloon 24 is then inflated and stent 26 is deployed (see FIG. 7). Balloon 24 is then deflated and catheter 10 is carefully withdrawn from the patient, leaving guidewires 104 and 106 in place (see FIG. 8) for further treatment of main vessel MV and branch vessel BV, should it be necessary. Additionally a branch stent could then be advanced over branch vessel guidewire 106 through side hole 28 of stent 26 into branch vessel BV, without compromising wire position in either main vessel MV or branch vessel BV.

Figure 9:
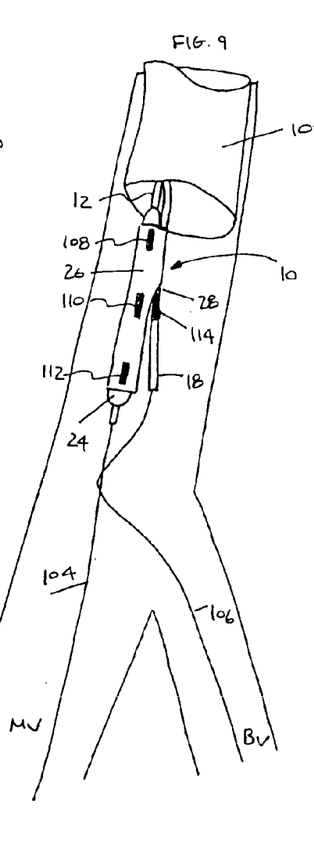
FIG. 9 illustrates the introduction of the catheter of FIG. 1 over the guidewires of FIG. 4, where the guidewires have become crossed.
Figures 10, 11, 12:
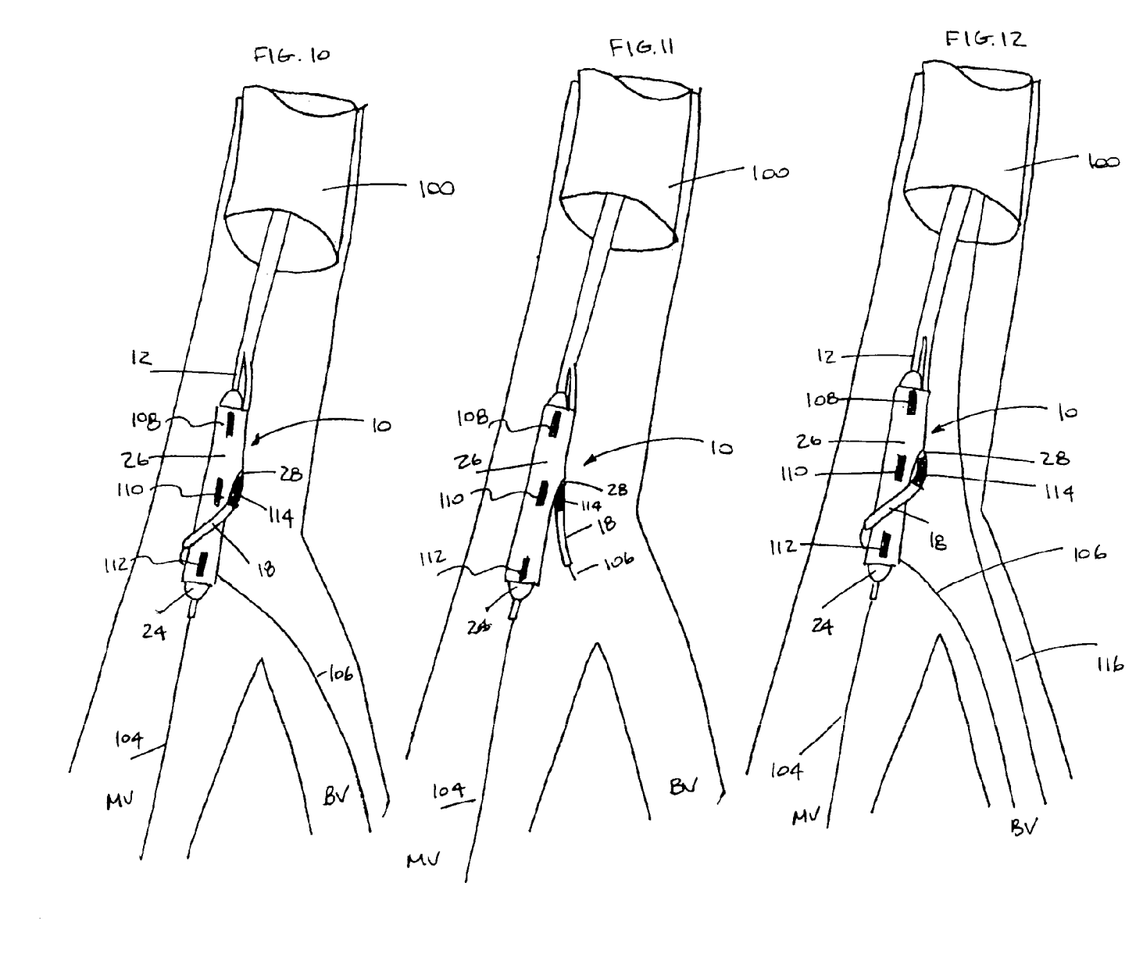
FIG. 10 illustrates the difficulty in advancing the catheter of FIG. 1 when the side member in FIG. 9 is incorrectly oriented and the guidewires have become crossed.
FIG. 11 illustrates the retraction of the branch vessel guidewire of FIG. 10 into the catheter to untangle the guidewires and to correctly orient the side member.
FIG. 12 illustrates the introduction of a backup branch vessel guidewire through a guiding catheter when the side member in FIG. 10 is incorrectly oriented and the guidewires have become crossed.

In some cases, crossing of main vessel guidewire 104 and branch vessel guidewire 106 may make it difficult for the physician to advance catheter 10 to the region of bifurcation (see FIG. 9). The wire crossing may prevent catheter 10 from smooth advancement beyond a certain point in main vessel MV and may cause guidewires 104 and 106 to buckle at distal end 102 of guiding catheter 100. Wire crossing may be observed using angiographic imaging. In some situations, because of guidewire crossing, side member 18 may become incorrectly oriented and may extend up and over stent 26, causing rotational tension in catheter 10 (see FIG. 10). If the physician feels that the wires are crossed, one option is to pull back branch vessel guidewire 106 just into side member 18 and thereby release rotational tension in catheter 10, orient side member 18 correctly and eliminate wire crossing (see FIG. 11). As illustrated in FIG. 11, when branch vessel guidewire 106 has been retracted into side member 18, it becomes uncrossed from main vessel guidewire 104. Although not shown, it will be appreciated that main vessel guidewire 104 could be retracted while branch vessel guidewire 106 remains in place. Once the wires have uncrossed and side member 18 has oriented itself correctly, branch vessel guidewire 106 may then be re-advanced back into branch vessel BV for final advancement of catheter 10 as illustrated in FIG. 6.

Figure 13:
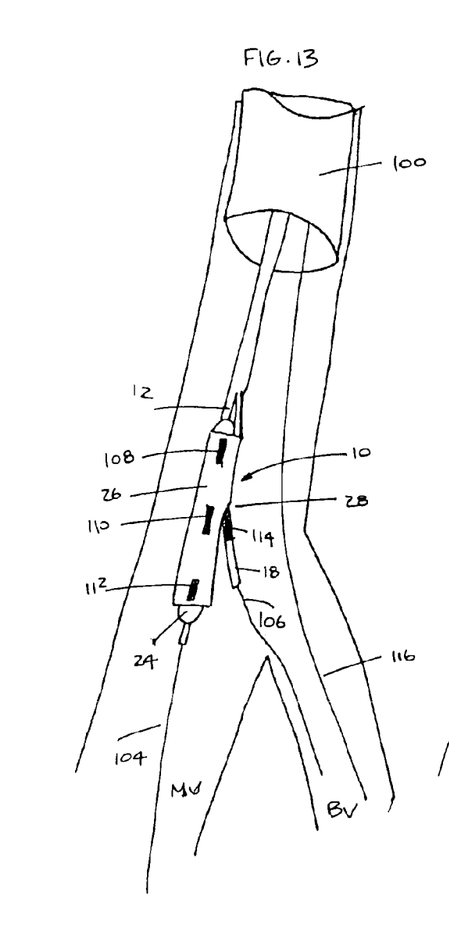
FIG. 13 illustrates the retraction of the branch vessel guidewire of FIG. 12 into the catheter and re-advancement back into the branch vessel to untangle the guidewires and to correctly orient the side member while a backup branch vessel guidewire is in the branch vessel.

In some cases, the physician will not wish to leave branch vessel BV unprotected without a guidewire in place. In such cases, the physician may optionally advance a backup branch vessel guidewire 116 into branch vessel BV prior to withdrawing branch vessel guidewire 106 (see FIG. 12). Backup branch vessel guidewire 116 passes through guiding catheter 100, but does not pass through catheter 10. Once backup branch vessel guidewire 116 is in place, branch vessel guidewire 106 may then be withdrawn into side member 18, as illustrated in FIG. 11. Once uncrossed, branch vessel guidewire 106 is then re-advanced back into branch vessel BV (see FIG. 13) for final advancement of catheter 10 as illustrated in FIG. 6. Backup branch vessel guidewire 116 is then withdrawn from branch vessel BV before deploying stent 26.

The use of a backup branch vessel guidewire permits the physician to have a guidewire in branch vessel BV at all times for protection and safety of the arteries in the event of procedural complications.

Figure 14:
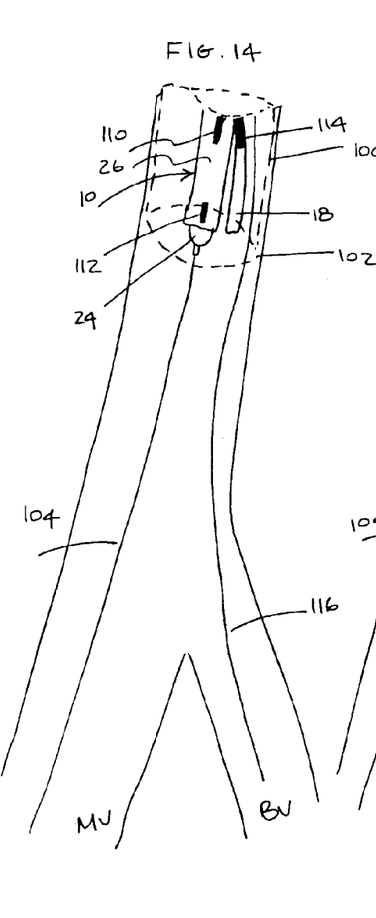
FIG. 14 illustrates another method for introducing the catheter of FIG. 1 by advancing the catheter over a main vessel guidewire until reaching the distal end of a guiding catheter, while a backup branch vessel guidewire is along side the catheter.
Figure 15:
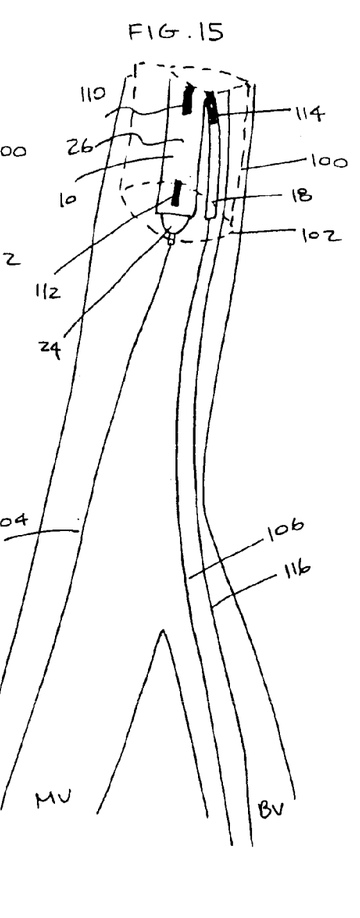
FIG. 15 illustrates the introduction of a branch vessel guidewire into the branch vessel in FIG. 14 by advancing the branch vessel guidewire through a side member of the catheter.

In some cases, due to size and tortuosity of main vessel MV and branch vessel BV, crossing of main vessel guidewire 104 and branch vessel guidewire 106 may be anticipated in advance of the intervention. In such a case, an alternative technique requiring a backup branch vessel guidewire 116 in addition to main vessel guidewire 104 and branch vessel guidewire 106 may be used. Such a technique is illustrated in FIGS. 14 and 15. Initially, guiding catheter 100 is introduced in a manner similar to that previously described. Main vessel guidewire 104 is then routed through guiding catheter 100 and down main vessel MV, past the bifurcation point and past the diseased section of main vessel MV. Backup branch vessel guidewire 116 is then inserted through guiding catheter 100, past the bifurcation point and past the diseased section of branch vessel BV. Catheter 10 is then loaded onto main vessel guidewire 104, outside of the patient's body. Main vessel guidewire 104 passes through lumen 30 (see FIG. 2) that extends through catheter body 12. Catheter 10 is advanced through guiding catheter 100 until reaching distal end guiding catheter 102 as illustrated in FIG. 14. Branch vessel guidewire 106 is then inserted into catheter 10 through branch vessel guidewire port 42 (see FIG. 3). Branch vessel guidewire 106 is then advanced to extend through side member 18, out of distal end 22 of side member 18 and is extended into branch vessel BV, leaving catheter 10 still sitting at distal end 102 of guiding catheter 100 as illustrated in FIG. 15. Catheter 10 is then pushed over guidewires 104 and 106 into the area of bifurcation until separation of marker 114 from marker 110 is observed in a manner similar to that previously described. Branch vessel guidewire 106 is withdrawn from branch vessel BV prior to deploying stent 26 in a manner similar to that previously described. Branch guidewire 106 is protected from crossing main vessel guidewire 104 through the length of catheter 10 as it travels in a dedicated branch guidewire lumen 34. The distance over which guidewires 104 and 106 may cross is thus limited to the length between distal end 102 of guiding catheter 100 and the bifurcation point. As previously described, this method minimizes the possibility of wire crossing. In the unlikely event of continued wire crossing, branch vessel guidewire 106 may be pulled back into side member 18 in a manner previously disclosed, ensuring that branch vessel BV is always protected by backup branch vessel guidewire 116. Alternatively, a backup wire may be placed in main vessel MV, and manipulation of main vessel guidewire 104 may be substituted in the steps previously described.

The invention has now been described in detail for purposes of clarity and understanding. However, it will be appreciated that certain modifications may be practiced within the scope of the appended claims.

What is claimed is:

1. A method for placing a stent having a side hole into a main vessel such that the side hole is aligned with an ostium of a branch vessel that extends from the main vessel, the method comprising:

inserting a main vessel guidewire into the main vessel until a distal end of the main vessel guidewire passes beyond the ostium of the branch vessel;

inserting a backup branch vessel guidewire into the main vessel until a distal end of the backup branch vessel guidewire passes into the branch vessel;

positioning a catheter system over the main vessel guidewire, the catheter system comprising a catheter body having a main vessel guidewire lumen and a branch vessel guidewire lumen, and a side member operably coupled to the catheter body, wherein the branch vessel guidewire lumen continues through the side member, wherein the catheter body includes at least one marker and the side member includes at least one marker, wherein the catheter body further includes a balloon with the stent being disposed over the balloon, wherein the side member extends into the stent and exits the stent through the side hole, and wherein the main vessel guidewire extends through the main vessel guidewire lumen;

advancing the catheter system over the main vessel guidewire until a distal end of the catheter body is near a distal end of a guiding catheter, and wherein the backup branch guidewire extends alongside the catheter system inserting a branch vessel guidewire through the branch vessel guidewire lumen of the catheter system until a distal end of the branch vessel guidewire passes into the branch vessel;

further advancing the catheter system over the main vessel guidewire and the branch vessel guidewire until the catheter body extends beyond the ostium and the side member extends into the branch vessel;

observing separation of the markers to indicate that the catheter body has passed beyond the ostium and the side member extends into the branch vessel using angiographic imaging;

withdrawing the backup branch vessel guidewire from the branch vessel;

inflating the balloon to deploy the stent within the main vessel, with the side hole being aligned with the ostium;

deflating the balloon; and withdrawing the catheter system from the main vessel and the branch vessel while leaving the main vessel guidewire and the branch vessel guidewire in place.

2. A method as in claim 1, wherein if the guidewires cross prior to final advancement of the catheter body, withdrawing the main vessel guidewire into the catheter body and re-advancing the main vessel guidewire back into the main vessel to uncross the guidewires and to correctly orient the side member.

3. A method as in claim 1, further comprising delivering a branch stent within the branch vessel through the side hole in the main stent.

4. A method as in claim 1, wherein if the guidewires cross prior to final advancement of the catheter body, withdrawing the branch vessel guidewire into the catheter body and re-advancing the branch vessel guidewire back into the main vessel to uncross the guidewires and to correctly orient the side member.

* * * * *